United States Patent [19]

Serafini et al.

[11] Patent Number: 5,149,772

[45] Date of Patent: Sep. 22, 1992

[54] HALOGENATED POLYIMIDE RESINS PREPARED BY ADDITION REACTIONS

[75] Inventors: Tito T. Serafini, Redondo Beach; Paul G. Cheng, Rancho Palos Verdes; Kenneth K. Ueda, Lomita; Ward F. Wright, Redondo Beach, all of Calif.

[73] Assignee: TRW Inc., Redondo Beach, Calif.

[21] Appl. No.: 824,090

[22] Filed: Jan. 22, 1992

Related U.S. Application Data

[63] Continuation of Ser. No. 472,036, Jan. 30, 1990, Pat. No. 5,091,505.

[51] Int. Cl.$^5$ .................... C08G 69/26; C08G 63/08; C08G 75/00; C08L 67/00
[52] U.S. Cl. .................... 528/353; 524/600; 524/879; 528/176; 528/288; 528/322; 528/342; 528/350; 528/352
[58] Field of Search ............... 528/176, 288, 322, 342, 528/350, 352, 353; 524/600, 879

[56] References Cited

U.S. PATENT DOCUMENTS

| | | | |
|---|---|---|---|
| 3,407,176 | 10/1968 | Loncrini | 528/185 |
| 3,459,706 | 8/1969 | Schweitzer | 528/128 |
| 3,505,295 | 4/1970 | Grunsteidl et al. | 528/322 |
| 3,745,149 | 1/1973 | Serafini et al. | 528/288 |
| 4,058,505 | 11/1977 | D'Alelio | 528/125 |
| 4,111,906 | 9/1978 | Jones et al. | 528/229 |
| 4,166,170 | 8/1979 | St. Clair | 528/229 |
| 4,189,560 | 2/1990 | Roth et al. | 526/259 |
| 4,203,922 | 5/1980 | Jones et al. | 528/185 |
| 4,391,967 | 7/1983 | Nimry et al. | 528/189 |
| 4,417,045 | 11/1983 | Nimry et al. | 528/188 |
| 4,456,653 | 6/1984 | Ruegg et al. | 428/379 |
| 4,801,682 | 1/1989 | Scola | 528/353 |

OTHER PUBLICATIONS

T. T. Serafini, P. Delvigs and G. R. Lightsey, Materials for '72, SAMPE, Azusa, Calif., 1972.
P. Delvigs, T. T. Serafini and C. F. Lightsey, Materials for '72, SAMPE, Azusa, Calif., 1972.
T. L. St. Clair and R. A. Jewell, NASA TM-74944, National Aeronautics and Space Administration, Washington, D.C., 1978.
T. T. Serafini and R. D. Vannucci, in Reinforced Plastics-Milestone 30, p. 14-E1, Society of Plastics Industry, Inc., New York, 1975, NASA TMX-71616.
T. T. Serafini, R. D. Vannucci and W. B. Alston, NASA TM-71894, National Aeronautics and Space Administration, Washington, D.C., 1976.
P. Delvigs, Investigation of a 700° F. Laminating Resin, Proceedings of Second Technical Conference on Polyimides, Ellenville, N.Y., Nov. 1985.
T. T. Serafini, Processable High Temperature Resistant Polymer Matrix Materials, Proceedings, ICCM I, vol. 1, AIME, New York, p. 202, 1976.
F. I. Hurwitz, Influence of Excess Diamine on Properties of PMR Polyimide Resins and Composites, NASA TMX-81580, 1980.
R. D. Vannucci, PMR Polyimide Compositions for Improved Performance at 371° C., NASA, SAMPE Apr. 6-9, 1987.
Matrix Resin Development, vol. II-Technical Proposal, Feb. 29, 1988.
First Technical Progress Report Entitled Matrix Resin Development from TRW to Northrop Corp. (Draft).
Technical Progress Report to Northrop Corp. from Jan. 16, 1989 to Feb. 15, 1989.
Submission to the General Electric Company for study entitled: Processable 700° F. Matrix Resins, Sep. 28, 1987.
Billmeyer, Jr., F., Textbook of Polymer Science, 2nd Ed., John Wiley and Sons, Inc., New York, p. 231.
Browning, C., New Applications from New Materials, in Margolis, J., Advanced Thermoset Composites, Van Nostrand Reinhold, New York, pp. 1-20.
Delvig, Peter et al., Addition-Type Polyimides from Solutions of Monomeric Reactants, NASA TN-6877, Aug. 1972.
Meares, P., Polymers Structure and Bulk Properties, D. Van Norstrand Company, Ltd., London, p. 265.
Serafini, T. et al., Highly Processable 371° C. (700° F.) Polyimides, 22nd International SAMPE Technical Conference, Boston, Mass., 1990.
Serafini, T., PMR Polyimide Composites for Aerospace Applications, in Polyimides, edited by K. L. Mittal, Penum Press, New York, pp. 957-975.
Vannucci, R., PMR Polyimide Compositions for Improved Performance at 371° C., SAMPE Quarterly, vol. 19, No. 1, Oct. 19, 1987, pp. 31-36.

Primary Examiner—John Kight, III
Assistant Examiner—T. Mosley
Attorney, Agent, or Firm—Jeffrey G. Sheldon; Sol L. Goldstein

[57] ABSTRACT

Polyimides having a high thermal and oxidative stability are prepared by reacting a mixture of monomers comprising (a) a dialkyl, trialkyl, or tetraalkylester of an aromatic tetracarboxylic acid, (b) an aromatic diamine, and (c) an end cap compound. The ratio of (a), (b), and (c) is chosen so that upon heating the mixtures, low molecular weight prepolymers are formed, the prepolymers having only one end cap radical and being suitable for chain extension and crosslinking to form high molecular weight, thermally stable polyimides. Upon heating, the prepolymers form polyimide resins, which can have $T_g$ in excess of 600° F. and superior physical properties.

28 Claims, No Drawings

HALOGENATED POLYIMIDE RESINS PREPARED BY ADDITION REACTIONS

This application is a continuation of U.S. patent application Ser. No. 472,036, filed Jan. 30, 1990, now U.S. Pat. No. 5,091,505. This application is related to U.S. patent application Ser. No. 7/824,089, filed on even date herewith, by the same inventors, and entitled, "POLYIMIDE RESINS PREPARED BY ADDITION REACTIONS," which is a continuation of U.S. patent application Ser. No. 472,198, which is incorporated herein by this reference.

BACKGROUND

This invention relates to polyimide resins, a class of organic compounds well known for their outstanding thermal-oxidative stability.

Polyimides are generally prepared either through direct condensation reactions to afford linear, long chain, polyimides, or through addition reactions performed on end-capped imide oligomers to give cross-linked polyimides. In both cases, it is well known that high stability is conferred by the use of aromatic or heteroaromatic moieties, while the use of aliphatic moieties reduces thermal-oxidative stability.

Condensation type polyimides have the highest thermal-oxidative stability because aliphatic end caps (which are used in addition type polyimides) are not used. Condensation type polyimides are typically prepared by treating an aryl dianhydride with an aryl diamine in an aprotic solvent to produce a polyamide acid, which is subsequently dehydrated to give the final linear polyimide. Substantial processing problems can arise during these manipulations. For example, the polyamide acid is prone to solvolytic degradation and thus its shelf life can be only a few hours at ambient temperature. Therefore, the polyamide acid requires special handling and storage under refrigeration, which creates inconveniences that greatly increase the ultimate cost to the user.

The dehydration step also creates processing difficulties. Dehydration can require prolonged heating under a vacuum to ensure complete removal of the aprotic solvent used in polyamide acid synthesis and the by-product, water. Alternatively, a chemical dehydration step can be used, but this requires use of large quantities of strong reagents such as mixture of acetic anhydride and pyridine. Isolation of the polyimide from the reaction mixture and solvent removal require laborious filtration and drying.

Other problems arise with condensation polyimides in one of their principal uses, namely composite materials comprising (i) the polyimide as a matrix material and (ii) fiber reinforcement. The reinforcement of condensation polyimides with fibers poses operational difficulties. High molecular weight polyimides have poor melt flow and must be processed under pressures of between 2000 to 6000 psi. Costs associated with fabricating parts under these conditions are prohibitive for most applications.

Alternatively, polyamide acid has been used to impregnate fibers, and the prepregs thus formed cured thermally to afford polyimide composites. However, because solvents and water are generated during curing, the fabricated parts exhibit excessive void contents resulting in inferior mechanical properties and reduced thermal-oxidative stability.

Processing problems associated with condensation type polyimides have been overcome through the use of addition polymerization type polyimides. Addition polyimides are commonly used in composite manufacturing because an intermediate oligomer (prepolymer) is formed, in situ, and the in situ-formed oligomers are easier to handle than the final polyimide. Furthermore, because no undesirable volatile materials are evolved during the final stage of polymerization, void-free parts can be fabricated. Addition type polyimide resins that are widely used for high temperature polymer matrix composites are typically made according to U.S. Pat. No. 3,745,149, which is incorporated herein by reference. This patent discloses a method for preparing polyimides from mixtures of (a) an dialkyl ester of an aromatic tetracarboxylic acid, (b) an aromatic diamine, and (c) an monoalkyl ester of a dicarboxylic acid (as an end cap) in a molar ratio of $n:(n+1):2$. The monomers are mixed in an alcoholic solvent, reacted at elevated temperatures to form, in situ, imide oligomers having end caps at both ends, and cured at high temperatures to yield macromolecular polyimides. Polyimide resins prepared by this method are conventionally referred to as PMR resins. Polyimide formulations prepared according to the method of U.S. Pat. No. 3,745,149, when reinforced with various fibers, have sufficient thermal stability and mechanical properties to serve as structural materials during continuous exposure at 550° F. These composites have successfully replaced metals as structural materials in applications such as jet engine cowls and ducts.

However, these addition type polyimides have two significant limitations. First, they are difficult to process. The selection of optimal formulations is restricted by the capability of standard composite fabrication equipment known as the autoclave. Autoclaves are typically constructed to withstand a maximal pressure of 200 to 300 psi only. It has been found that the prepolymers prepared under this patent cannot have a formulated molecular weight of much greater than 1500, beyond which void-free parts cannot be readily autoclaved. Second, such formulations have an aliphatic content of 12% or greater because of the presence of the aliphatic end cap groups. The high aliphatic content can result in severe degradation at higher temperature, thus limiting the high temperature applicability of PMR polyimide resins.

Much interest exists in developing addition type polyimides that can be used at 600° to 800° F. However, with the current technology, better thermal-oxidative stability cannot be accomplished without compromising processability. The adoption of PMR polyimides to a higher temperature range is therefore not economically feasible at present.

In particular, attempts to prepare polyimides that can be used at temperatures above 550° F. according to the methodology described in U.S. Pat. No. 3,745,149 have been unsuccessful. See, for instance, R. Vanucci, *SAMPE Quarterly,* 19, (1), 31 (1987) and references cited therein. Typically, attempts have been made to synthesize higher molecular weight (about 3000) imide oligomers to minimize the contents of the aliphatic end-caps and thereby improve the thermal-oxidative stability. However, as the molecular weights of the imide oligomers increase, the resin flow decreases. Polyimides formulated according to U.S. Pat. No. 3,745,149 and having molecular weights high enough to withstand long term exposure at 700° F. in air have been found to require pressures of between 2000 and 5000 psi for proper consolidation. The processing of conventional high molecular weight imide oligomers thus can not be conducted with autoclaves, a hurdle that renders polyimides prepared according to U.S. Pat. No. 3,745,149 impractical for use at temperatures substantially above 550° F.

Accordingly, there is a need for compositions of matter and methods for preparing addition type polyimide resins, where the resins are easily prepared, composites containing the resins can be prepared using conventional autoclave equipment, and the resins have the capability of extended operation at elevated temperatures of at least 600° F.

SUMMARY

The present invention provides polyimide resins and methods for their manufacture that satisfy these needs. Polyimide resins prepared in accordance with the present invention not only have high temperature capability, but have been found to have processability and physical properties superior to those of prior art addition type polyimide resins.

A composition of matter suitable for preparing these polyimide resins consists essentially of a mixture of the monomers:

(a) a dialkyl or tetraalkylester of an aromatic tetracarboxylic acid;

(b) an aromatic diamine; and (c) a divalent end cap compound characterized by (i) having at least one unsaturated moiety, (ii) being capable of reacting with the aromatic diamine or the ester to form an end cap radical that precludes further reaction of the aromatic diamine with the ester, and (iii) being capable of undergoing addition polymerization.

The molar ratio of (a), (b), and (c) is such that heating the mixture forms low molecular weight prepolymers having only one end cap radical and suitable for chain extension and crosslinking to form high molecular weight, thermally stable polyimides. Typically the prepolymers have a molecular weight of from about 2000 to about 10,000. When the end cap reacts with the diamine, the molar ratio of a:b:c is n:n:1, where n is at least 2 and is sufficiently small, generally less than about 20, that the molecular weight of the prepolymer is less than about 10,000. When the end cap reacts with the ester, the molar ratio of a:b:c is (n+1):n:1.

The formula of the prepolymers depends upon whether the end cap compound reacts with the diamine or the ester. Where the end cap compound reacts with diamine, the prepolymers have the formula:

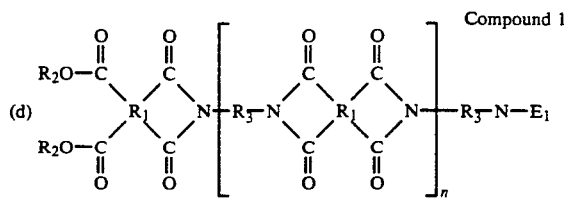

Compound 1 where the end cap compound reacts with the ester, the prepolymers have the formula:

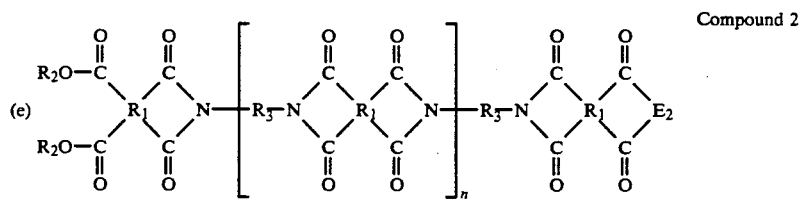

Compound 2

In these formulas:

$R_1$ is a tetravalent aryl radical provided by the tetracarboxylic acid, each $R_2$ is independently selected from the group consisting of alkyl and hydrogen, at least one $R_2$ being alkyl, $R_3$ is a divalent aryl radical provided by the aromatic diamine, and $E_1/E_2$ is the end cap radical provided by the end cap compound, the end cap radical having at least one unsaturated moiety and being capable of undergoing addition polymerization. Only one of prepolymer (d) and prepolymer (e) is present, and thus only one of $E_1$ and $E_2$ is present. These prepolymers are new compounds.

The composition of matter can include an organic solvent, where the monomers comprise about from about 30 to about 90 percent by weight of the solution.

A process for preparing the polyimide resin from the monomer composition comprises heating the monomer composition to a sufficiently high temperature to remove the solvent, and then heating the composition to at least about 375° F. to obtain the polyimide prepolymers. Then the prepolymers are heated to a temperature of at least about 690° F. to obtain polyimide resins having an average molecular weight in excess of 10,000. Preferably the polymers are postcured at a temperature of at least about 650° F., and preferably from about 700° to about 750° F., for at least 12 hours to enhance the physical properties of the polyimide resin.

The polyimide resins can be formed into complex shapes using autoclave and molding equipment, including with prepolymers having molecular weights in the order of 5,000 to 6,000. Polyimide resins of this invention have better physical properties than those of prior art addition type polyimide resins prepared from the same materials, including higher glass transition temperature ($T_g$), high temperature stability, and better toughness. For example, $T_g$'s greater than 700° F. have been achieved. In addition, the new polyimide resins can exhibit a weight loss of substantially less than 10% when heated in air at 700° F. for 100 hours. Accordingly, composites comprising fibers reinforcing these polyimide resins can be used in high temperature applications for which addition type polyimide resins have heretofore been unsatisfactory or too expensive.

DESCRIPTION

According to this invention, high temperature polyimides are synthesized from a mixture of the following monomer compounds:

(a) 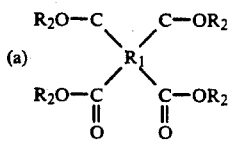   Compound 3 wherein $R_1$ is a tetravalent aryl moiety and $R_z$ is alkyl, normally lower alkyl of one to four carbon atoms, or hydrogen, at least two of $R_2$ being alkyl;

(b) 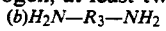   Compound 4 wherein $R_3$ is a divalent aryl moiety; and (c) a divalent end cap compound characterized by (i) having at least one unsaturated moiety, (ii) being capable of reacting with the aromatic diamine or the ester to form an end cap radical that precludes further reaction of the aromatic diamine with the ester, and (iii) being capable of undergoing addition polymerization.

Esters

The esters of tetracarboxylic acid of Compound 3 can be prepared readily from the corresponding dianhydrides of the formula:

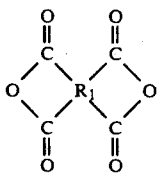   Compound 5 in which $R_1$ is as defined above. Representative of the many dianhydrides which may be employed are those disclosed in Table I of U.S. Pat. No. 4,111,906, which is incorporated herein by reference. The dianhydrides listed in Table I are:

pyromellitic dianhydride benzophenone tetracarboxylic dianhydride
2,3,6,7-naphthalene tetracarboxylic dianhydride
3,3',4,4'-diphenyl tetracarboxylic dianhydride
1,3,5,6-naphthalene tetracarboxylic dianhydride
2,2',3,3'-diphenyl tetracarboxylic dianhydride
2,2-bis(3,4-dicarboxyphenyl)propane dianhydride
3,4,9,10-perpylene tetracarboxylic dianhydride
bis(3,4-dicarboxyphenyl)ethere dianhydride
ethylene tetracarboxylic dianhydride
naphthalene-1,2,4,5-tetracarboxylic dianhydride
naphthalene-1,4,5,8-tetracarboxylic dianhydride
decahydronaphthanlene-1,4,5,8-tetracarboxylic dianhydride
4,8-dimethyl-1,2,3,5,6,7-hexahydronaphthalene-1,2,5,6-tetracarboxylic dianhydride
2,6-dichloronaphthalene-1,4,5,8-tetracarboxylic dianhydride
2,7-dichloronaphthalene-1,4,5,8-tetracarboxylic dianhydride
2,3,6,7-tetrachloronaphthalene-1,4,5,8-tetracarboxylic dianhydride
phenanthrene-1,8,9,10-tetracarboxylic dianhydride
cyclopentane-1,2,3,4-tetracarboxylic dianhydride
pyrrolidine-2,3,4,5-tetracarboxylic dianhydride
pyrazine-2,3,5,6-tetracarboxylic dianhydride
2,2-bis(2,3-dicarboxyphenyl)propane dianhydride
1,1-bis(2,3-dicarboxyphenyl)ethane dianhydride
1,1-bis(3,4-dicarboxyphenyl)ethane dianhydride
bis(2,3-dicarboxyphenyl)methane dianhydride
bis(3,4-dicarboxyphenyl)sulfone dianhydride
benzene-1,2,3,4-tetracarboxylic dianhydride
thiophene-2,3,4,5-tetracarboxylic dianhydride.

Particularly suitable dianhydrides include pyromellitic dianhydride, 3,3',4,4'-benzophenone tetracarboxylic dianhydride, 2,2',3,3'-diphenyl tetracarboxylic dianhydride, bis (3,4-dicarboxyphenyl) ether dianhydride, 2,2-bis (3,4-dicarboxyphenyl) hexafluoropropane dianhydride. Other dianhydrides suitable are the fluorinated anhydrides described in U.S. Pat. No. 4,801,682, which is incorporated herein by this reference namely 4,4'(2,2,2-trifluoro-1-phenylethylidene)-biphthalic tetracarboxylic acid dianhydride.

Diamines

Representative diamines of the type of Compound 4 defined above are p-phenylenediamine, m-phenylenediamine, 4,4'-methylenedianiline, 4,4'-diaminodiphenylsulphone, 4,4'-oxydianiline.

A particular advantageous feature of the present invention is that diamines that have generally not been used for forming polyimide resins due to unsatisfactory temperature characteristics can now be used. For example, in the present invention is it possible to use phenylenediamine in place of the more toxic 4,4'-methylenedianiline, without sacrificing the physical properties of the final product. In other words, polyimide resins prepared according to the present invention using p-phenylenediamine as the diamine have physical properties and temperature resistance comparable to prior art polyimide resins prepared with 4,4'-methylenedianiline, without the danger of toxicity associated with the latter diamine.

End Cap

The end cap compounds control the average molecular weight of oligomers or prepolymers formed by condensation polymerization of the ester (a) and diamine (b) by reacting with either the ester or diamine. When the end cap compound reacts with the diamine to produce $E_z$, the end cap compound can be:

   Compound 6 wherein $R_2$ is defined as above, and wherein at least one of $R_2$ is alkyl, and $R_4$ is a divalent radical of the formulas:

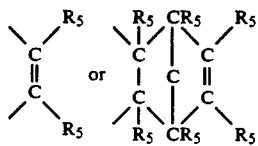   Compounds 7, 8

Where each $R_5$ is independently selected from the group consisting of hydrogen and lower alkyls, normally one to four carbon atoms.

In this version of the invention, the mono- or dialkyl ester of the dicarboxylic acid defined in the preceding formula can be prepared from the corresponding anhydride of the formula:

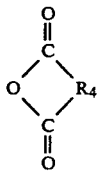

wherein $R_4$ is as defined above. Representative of such dianhydrides include maleic anhydride, citraconic anhydride, 5-norbornene-2,3-dicarboxylic anhydride, and alkyl or alkenyl substituted 5-norbornene-2,3-dicarboxylic anhydride.

Suitable end cap compounds for reacting with the ester to produce $E_z$ are amino compounds have a moiety capable of addition polymerization. These include p-ethynylaniline (p-aminophenyllacetylene), p-aminostyrene, and 4-aminobenzocyclobutene.

The ester, diamine, and end cap compound are dissolved in an organic solvent. Representative of useful solvents are aliphatic alcohols, aliphatic ethers, N,N-dimethylformamide, and dimethylsulfoxide. Mixtures of two or more of such solvents can be employed. The solvents are inert to the monomers. The solutions of the esters and diamine have excellent shelf stability.

Preparation of Polyimides

To prepare polyimides from this mixture of monomers, first the mixture is heated to a sufficiently high temperature to evaporate the solvent, generally in the order of about 120° F. to about 250° F. Then the mixture is heated to a sufficiently high temperature to form the prepolymers, generally a temperature of at least about 375° F.

When the end cap compound reacts with the diamine, the molar ratios of the ester, diamine, and end cap compound are n:n:1, and the prepolymer formed is believed to have the formula:

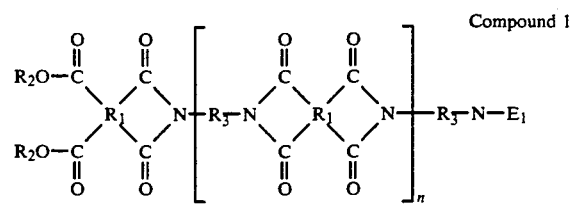

Compound 1

Where the end cap compound reacts with the ester, the molar ratio of the ester, diamine, and end cap compound is (n+1):n:1, and the prepolymer formed is believed to have the formula:

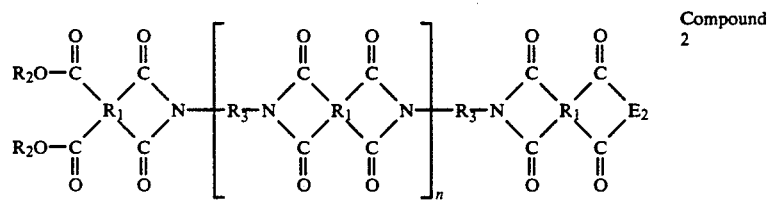

Compound 2

A preferred version of the invention where the end cap compound is compound 6 defined above results in a prepolymer having the formula:

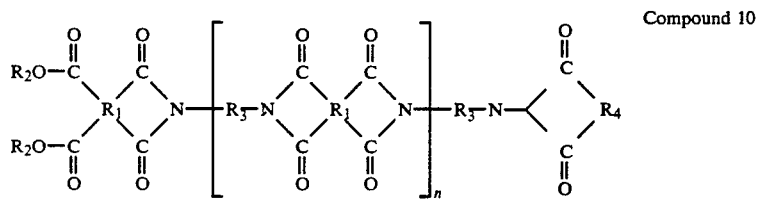

Compound 10

In all cases, $R_1$, $R_3$, $R_4$, n, $E_1$ and $E_2$ are as defined above.

Macromolecular polyimides having a molecular weight greater than 10,000 are prepared when the imide prepolymers are heated at elevated temperature, generally at least about 690° F., and typically in the range of from about 700° to about 750° F. Heating takes place for a sufficient time to form a crosslinked and thermally stable polyimide resin having an average molecular weight in excess of 10,000.

Preferably the polyimide resin is postcured by heating in air at a temperature of at least about 650° F., and preferably from about 700° to about 750° F., for at least 7 hours.

Applications

Polyimide resins of the present invention have many applications. For example, they can be reinforced with fiber to make structural components such as aircraft engines and air frames. Among the fiber materials that can be used are carbon, including graphite; ceramics, including glass, quartz, alumina, and silica; silicon carbide; and refractory metals such as tungsten.

Another application for the polyimide resins is use as an adhesive, particularly as adhesives for joining composite structures made of polyimide resins.

The polyimide resins can also be used for molding, such as by injection molding or resin transfer molding. They can also be used as a protective coating for providing protection against high temperatures and/or oxidizing conditions.

Advantages

Polyimides resins have been successfully prepared from the prepolymers of Compound 10. This is very surprising. It has long been conventional wisdom that to form polyimide resins, it is necessary to have an unsaturated end cap on both ends of the prepolymer, where the end caps can undergo a vinyl type addition polymerization. It is very surprising to find that these oligomers, through some unknown reaction mechanism, crosslink and polymerize to form polyimide resins. Not to be bound by theory, it is believed that crosslinked polyimide resins are formed because pendent anhydride residues participate in crosslinking, thereby enhancing the properties of the polyimide resins.

Moreover, as detailed below, it was surprising to learn that the polyimide resins of the present invention have better temperature stability and better physical properties than comparable PMR resins. Moreover, the oligomers formed by the method of the present invention are easier to process than the oligomers of the PMR process. Thus, higher weight oligomers can be used, such as in the molecular weight range of 3,000 to 5,000, compared to the generally accepted limit of about 1,500 for PMR resins processed using conventional autoclave equipment.

In particular, an important advantage of the present invention is that the imide oligomers formed have markedly better rheological properties than the PMR polyimide resins prepared according to U.S. Pat. No. 3,745,149. For example, imide oligomers prepared according to that Patent and having a formulated molecular weight of about 3000 need to be processed under a pressure of 2000 psi. In contrast, imide oligomers formulated with the methods disclosed herein and having a formulated molecular weight of 4800 were satisfactorily processed under a pressure of 200 psi. Thus, the superior rheological properties allow imide oligomers of potentially much higher formulated molecular weight to be processed with existing industrial equipments.

The present invention offers a second advantage in reducing the contents of the less stable aliphatic endcap content. Compared to the doubly end-capped imide oligomers made according to U.S. Pat. No. 3,745,149, imide oligomers with the same formulated molecular weight but prepared according to the present invention have their aliphatic contents reduced by one-half because there is only one aliphatic end cap present Moreover, since the molecular weight of the oligomer can be more than doubled without sacrificing processing characteristics, this provides another 50% decrease in the aliphatic content of imide oligomers according to the present invention compared to the PMR oligomers. Thus, the aliphatic content of the polyimide resins prepared according to the present invention can be less than 25% of the aliphatic content of PMR resins.

Taken together, the two advantages described above allow facile fabrication of polyimides from imide oligomers that have high molecular weight and very low aliphatic content. For example, imide oligomers of formulated molecular weight of 3800 to 4800 can be processed readily. These materials, because of their high molecular weight and their being capped on one end only, can have aliphatic content of only 1.8% to 2.4% by weight. Because of the low aliphatic content, these polyimides have excellent stability even after prolonged heating in air at temperatures of 600° F. or higher. Therefore, the present invention expands the application of polyimide composite technology to temperatures substantially above 550° F., the current practical limit, without resorting to expensive processing equipment.

A third advantage of the present invention relates to the glass transition temperature of polyimide resins. Above its glass transition temperature, a polymer loses much of its rigidity. Therefore, for a polymer composite to be useful as structural material, the resin's glass transition temperature must exceed the intended use temperature. Polyimides usually have glass transition temperatures of between 600° to 650° F. (as determined by the dynamic storage modulus, G', curve inflection point from dynamic mechanical analysis). When conventional addition polyimides are heated in air, typically at 700° F. or higher, their glass transition temperature can be increased moderately. However, glass transition temperatures cannot be raised much above 700° F. because substantial degradation occurs. The difficulty in attaining high glass transition temperatures thus also impedes the use of polyimide composites as load-bearing materials at temperatures above 700° F. The glass transition temperatures of polyimides prepared under the present invention, in contrast, rapidly increase upon heating and are as high as 700° F. after postcure.

All values for $T_g$ reported herein were obtained by measuring the inflection points of the dynamic storage modulus (G') curves obtained by means of dynamic mechanical analysis using ASTM D4065-82.

A fourth advantage of the present invention relates to the improved processability of the oligomers. Oligomers according to the present invention have much better rheological characteristics than PMR oligomers. Thus, they can be used for forming complex shapes. If an oligomer according to the present invention having a molecular weight of 1500 is used, it has a substantially better processability than the corresponding PMR oligomer having a molecular weight of 1500. Thus, the oligomers of this invention can be used to form complex parts having temperature stability and physical properties comparable to those of a less complex part formed from PMR resins.

The following examples describing certain representative embodiments of the present invention.

EXAMPLE 1

MOLDING POWDER

A suspension of benzophenone dianhydride (32.2 g, 0.1 mole) in 30 mL of methanol was heated at reflux temperature with stirring until the solid dissolved, and then for an additional 2 hours to yield a methanolic solution of the corresponding diester-diacid. A suspension of nadic dianhydride (1.64 g, 0.01 mole) in 5 mL of methanol was heated at reflux temperature with stirring until the solid dissolved, and then for an additional period of 1 hour to afford a solution of the corresponding monoester-monoacid. To a suspension of methylenedianiline (19.8 g, 0.1 mole) in 50 mL of methanol there was first added the diester-diacid solution, followed by the monoester-monoacid solution to form a solution containing diester-diacid : diamine : monoester-monoacid in 10:10:1 molar ratio.

The methanolic solution of the monomeric reactants was concentrated on a hotplate, and heated in an air-circulating oven at 204° C. (400° F.) for 1 hour to form powdered imide oligomers having a formulated molecular weight of 5000. A stainless steel mold was treated with mold release agent (Frekote 44 ™ fluorinated hydrocarbon based agent obtained from Frekote, Inc., located in Boca Raton, Florida), and charged with 1.01 g of the imide oligomer powder. The mold assembly was placed in a hydraulic press and heated to 274° C. (525° F.) upon which a pressure of 83 psi was applied. The mold temperature was increased to 329° C. (625° F.), and then the applied pressure was increased to 1000 psi. This pressure was maintained throughout the remainder of the molding cycle. The mold temperature was then increased to 371° C., held at 371° C. (700° F.) for 1 hour, and allowed to cool to room temperature to afford a pliable neat resin bar for testing.

Tg of the as-molded specimen was 280° C. (536° F.), and increased to 320° C. (608° F.) after postcuring in air for 16 hours at 650° F. A 0.45 gram sample was heated in air at 700° F. for 76 hours upon which the Tg increased to 350° C. (662° F.). The weight loss was approximately 7.8% during the 76 hour exposure.

EXAMPLE 2
PREPREG WITH CARBON FIBERS

A mixture of 37.3 g (0.084 mole) of 4,4'-(hexafluoroisopropylidene)-bis(phthalic anhydride) and 30 mL of anhydrous methanol was heated at reflux and stirred until the solid dissolved, and then for an additional two hours to afford a methanolic solution of dimethyl 4,4'-(hexafluoroisopropylidene)-bis(phthalate) (6-FDE). A mixture of 1.97 g (0.012 mole) of 5-norbornene 2,3-dicarboxylic anhydride and 5 mL of anhydrous methanol was heated at reflux and stirred until the solid dissolved, and then for an additional hour to afford a methanolic solution of methyl 5-norbornene 2,3-dicarboxylate (NE). The methanolic solution of 6-FDE was slowly added to a suspension of p-phenylenediamine (9.1 g, 0.084 mole) in 30 mL of anhydrous methanol, and the resulting homogeneous solution was then treated with the methanolic solution of NE to afford a monomeric reactant solution containing an diester-diacid : diamine : monoester-monoacid molar ratio of 7:7:1.

Prepreg tapes were made by drum winding Celion 300 $_{TM}$ carbon fiber (obtained from American Cyanimid) and impregnating the fiber with the monomeric reactant solution. The prepreg tapes were heated at 68° C. for one hour to remove most of the methanol to afford a flexible tape. It was possible to easily cut and shape the tape into various forms.

A separator film of Armalon $_{TM}$ fluorocarbon/glass cloth from DuPont of Wilmington, Delaware, was placed in a stainless steel mold. Twelve plies of these 2 by 4 inches prepreg tapes were placed on top of the film and heated at 204° C. (about 400° F.) for one hour, whereupon the monomers in the fiber reacted to form imide oligomers having a formulated molecular weight of 3800. At the same time, the volatile products of the reaction and residual methanol were evaporated.

A second separator film was placed on top of the prepreg tapes and the mold was closed, placed in a press and heated to 240° C. upon which a pressure of 200 psi was applied and maintained throughout the remainder of the molding cycle. The temperature was then raised to 316° C. (about 600° F.) over a period of 30 minutes, held at that temperature for two hours and then allowed to cool to room temperature. The resulting laminate was postcured in air without applied pressure at about 316° C. for 16 hours, about 344° C. for four hours, about 357° C. for four hours, about 371° C. for four hours, about 385° C. for 4 hours, and about 399° C. for 2 hours. The resulting carbon-polyimide composite was essentially void-free as analyzed by ultrasonic C-scanning and scanning electron microscopic inspection of a polished surface.

The glass laminate was subsequently postcured at 600° F. for 20 hours and 700° F. for 7 hours. The postcured laminate had a glass transition temperature of 372° C. (702° F.).

EXAMPLE 3
PREPREG WITH QUARTZ FIBER

Using the method of Example 2, Astroquartz TM (J.P. Stevens of Slater, South Carolina) quartz fiber laminates were produced. The resin composed about 30% by weight of the laminate. The non-postcured laminate had a flexural strength (tested with a universal testing instrument in accordance with ASTM D-790 using a three-point loading fixture with a span/depth ratio of 16) of 157 ksi and an interlaminear shear strength (measured in accordance with ASTM D-2344 using a three-point variable span fixture and a span/depth ratio of 4) of 9.8 ksi at room temperature and 7.5 ksi at 700° F. When the laminate specimen was heated for 100 hours at 700° F. in an air-circulating oven, the weight loss of the laminate was about 1.8%.

A sample of the laminate was postcured at 700° F. for 100 hours. The postcured sample exhibited a flexural strength of 154 ksi at room temperature and 8.5 ksi interlaminear strength of 8.5 ksi at room temperature.

EXAMPLE 4
PROSPECTIVE EXAMPLE USE AS AN ADHESIVE

A scrim cloth is impregnated with a methanolic solution of the polyimide prepared according to Example 2 and the solvent is removed by evaporation at 68° C.. The process is repeated until a 10 mil thickness is achieved. This cloth is then placed between two titanium panels whose surfaces have been cleaned and primed with a very dilute solution of the polyimide from which the solvent has been removed. This assembly is heated under contact pressure at 204° C. for 1 hour, placed in a vacuum bag and evacuated at full vacuum. The bag is heated to 430° F. and placed under 200 psi autoclave pressure. The temperature is then brought to 700° F. at 5° F. a minute, held at 700° F. for 4 hours, and cooled to ambient temperature.

EXAMPLE 5
PROSPECTIVE EXAMPLE, USE AS A HEAT PROTECTIVE COATING

A methanolic solution of the polyimide prepared according to the procedure of Example 2 is sprayed on panels prepared from conventional PMR additive type polyimide resins. The solvent is removed at 68° C.. This procedure is repeated until a coating thickness of 3 mil is achieved. The coated panel is heated at 204° C. for 1 hour and brought to 316° C. at 3° C. a minute, held at 316° C. for 2 hours, and then postcured at 371° C. for 2 hours.

Although the present invention has been described in considerable detail with regard to the preferred versions thereof, other versions are possible. Therefore, the appended claims should not be limited to the descriptions of the preferred versions contained herein.

What is claimed is:
1. A composition of matter consisting essentially of low molecular weight prepolymers substituted with a halogen selected from the group consisting of chlorine and fluorine, the prepolymers having only one end cap radical and suitable for chain extensions and crosslinking to form high molecular weight, thermally stable polyimides, the prepolymers having the formula:

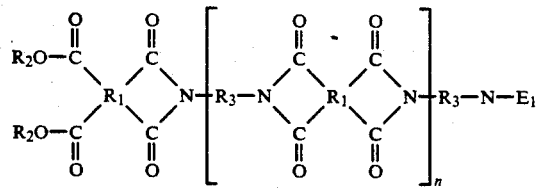

where
R$_1$ is a tetravalent aryl radical,
each R$_2$ is independently selected from the group consisting of alkyl and hydrogen, at least one R$_2$ being alkyl,
R$_3$ is a divalent aryl radical,
E$_1$ is an end cap radical having at least one unsaturated moiety and being capable of undergoing addition polymerization, and
n is at least 2 and is sufficiently small that the average molecular weight of the prepolymers is less than about 10,000.

2. A composition of matter consisting essentially of low molecular weight prepolymers substituted with a halogen selected from the group consisting of chlorine and fluorine, the prepolymers having only one end cap radical and suitable for chain extension and crosslinking each R$_2$ is independently selected from the group consisting of alkyl and hydrogen, at least one R$_2$ being alkyl,
R$_3$ is a divalent aryl radical,
E$_2$ is an cap radical having at least one unsaturated moiety and being capable of undergoing addition polymerization, and
n is at least 2 and is sufficiently small that the average molecular weight of the prepolymers is less than about 10,000.

3. A composition of matter consisting essentially of a mixture of the monomers:
(a) a dialkyl, trialkyl, or tetraalkylester of an aromatic tetracarboxylic acid, the ester being substituted with a halogen selected from the group consisting of fluorine and chlorine;
(b) an aromatic diamine; and
(c) a divalent end cap compound characterized by (i) having at least one unsaturated moiety, (ii) being capable of reacting with the aromatic diamine or the ester to form an end cap radical that precludes further reaction of the aromatic diamine with the ester, and (iii) being capable of undergoing addition polymerization,
wherein the ester (a), aromatic diamine (b), and end cap compound (c) are present in a molar ratio such that heating the mixture forms low molecular weight prepolymers having only one end cap radical and suitable for chain extension and crosslinking to form high molecular weight, thermally stable polyimides, the prepolymers having the formula of either;

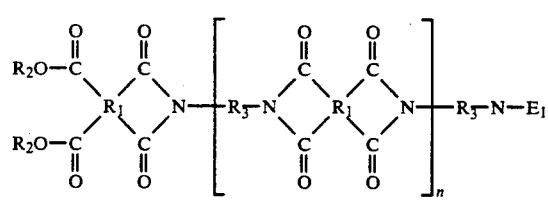 (d)

or

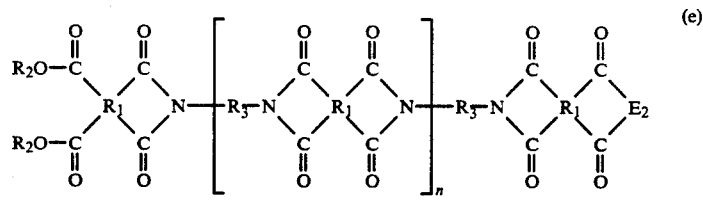 (e)

to form high molecular weight, thermally stable polyimides, the prepolymers having the formula:

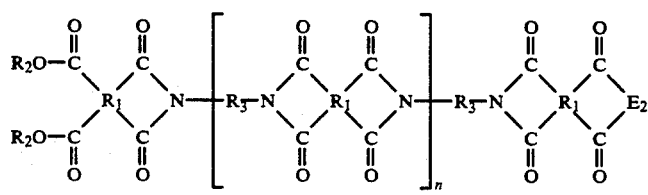

where
R$_1$ is a tetravalent aryl radical, where
R$_2$ is a tetravalent aryl radical provided by the tetracarboxylic acid,
each R$_2$ is independently selected from the group consisting of alkyl and hydrogen, at least one R$_2$ being alkyl, $R_3$ is a divalent aryl radical provided by the aromatic diamine, $E_1$ is an end cap radical provided by the end cap compound when the prepolymers are of formula (d), and $E_2$ is an end cap radical provided by the end cap compound when the prepolymers are of formula (e), the end cap radicals having at least one unsaturated moiety and being capable of undergoing addition polymerization, and n is at least 2 and is sufficiently small that the average molecular weight of the prepolymers is less than about 10,000.

4. A composition of matter consisting essentially of a mixture of compounds of the formulas:

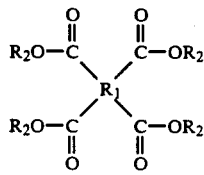 (a)

wherein $R_1$ is a tetravalent aryl radical substituted with a halogen selected from the group consisting of chlorine and fluorine, and each $R_2$ is independently selected from the group consisting of alkyl and hydrogen; and at least two $R_2$ are alkyl;

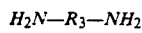 (b)

wherein $R_3$ is a divalent aryl radical; and

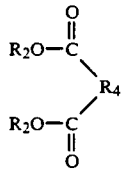 (c)

wherein $R_2$ is as defined in (a) and at least one $R_2$ is alkyl, and $R_4$ is a divalent radical of the formula:

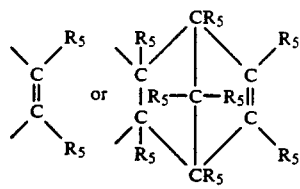

wherein each $R_5$ is independently selected from the group consisting of hydrogen and lower alkyls; and wherein the molar ratio of a:b:c: is n:n,1, wherein n is of from 2 to about 20.

5. A polyimide resin having a molecular weight greater than 10,000 prepared by crosslinking the prepolymers of claim 1 or 2.

6. An article of manufacture comprising fibers impregnating a polyimide resin matrix having a molecular weight greater than 10,000 and prepared by crosslinking the prepolymers of any one of claims 1-4.

7. Fibers coated with the composition of matter of claim 1, 2, 3 or 4.

8. The polyimide resin of claim 5 having a $T_g$ greater than 600° F.

9. The polyimide resin of claim 8 having a weight loss of less than 10% when heated in air at 700° F. for 100 hours.

10. The invention of claim 1 or 3 wherein the end cap compound is:

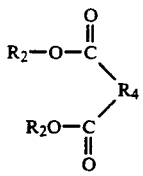

wherein
each $R_2$ is independently selected from the group consisting of alkyl and hydrogen and at least one $R_2$ is alkyl, and
$R_4$ is a divalent radical of the formula:

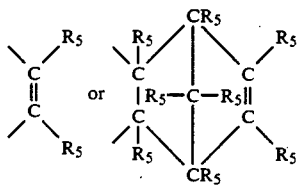

wherein each $R_5$ is independently selected from the group consisting of hydrogen and lower alkyls.

11. The invention of claim 1, 2, 3, or 4 wherein the prepolymers have a molecular weight greater than 3,000 and are capable of flowing during heat processing to remove voids at temperature less than about 500° F. and pressures less than about 200 psi.

12. A process for preparing polyimide resin comprising the steps of:
(1) reacting, by heating to at least about 375° F., a mixture of:
(a) an ester having the formula:

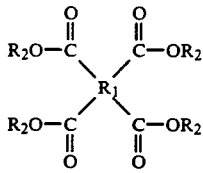

wherein $R_1$ is a tetravalent aryl radical substituted with a halogen selected from the group consisting of chlorine and fluorine and $R_2$ is alkyl or hydrogen, and at least two of $R_2$ are alkyl,
(b) an aromatic diamine of the formula [₂N—R-3—NH₂] NH₂—R₃—NH₂ wherein $R_3$ is a divalent aryl radical; and
(c) a divalent end cap compound characterized by (i) having at least one unsaturated moiety, (ii) being capable of reacting with the aromatic diamine or the ester to form an end cap radical that precludes further reaction of the aromatic diamine with the ester, and (iii) being capable of undergoing addition polymerization, wherein the ester (a), aromatic diamine (b), and end cap compound (c) are present in a molar ratio such that the mixture forms low molecular weight polyimide prepolymers having an ester (a) end group and only one end cap radical, the prepolymers being suitable for chain extension and crosslinking to form high molecular weight, thermally stable polyimides, the polyimide prepolymers having an average molecular weight in the range of about 2000 to about 10,000; and (2) heating the prepolymers to a temperature of at least about 690° F. to obtain polyimide resins having an average molecular weight in excess of 10,000.

13. A process for preparing polyimide resins comprising the steps of:

(1) reacting, by application of heat to at least about 375° F., a mixture of compounds of the formulas:

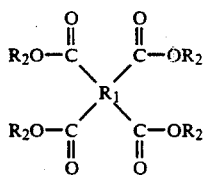
(a)

wherein $R_1$ is a tetravalent aryl radical substituted with a halogen selected from the group consisting of chlorine and fluorine, and $R_2$ is alkyl or hydrogen, and at least two of $R_2$ are alkyl,

(b)

wherein $R_3$ is a divalent aryl radical; and

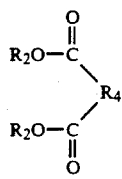
(c)

wherein $R_2$ is as defined in (a) and at least one $R_2$ is alkyl, and $R_4$ is a divalent radical of the formula:

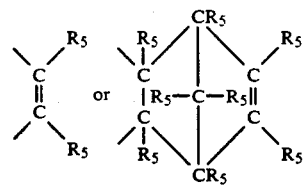

wherein $R_5$ is a hydrogen or lower alkyl, and wherein the molar ratio of a:b:c is n:n:1, wherein n is from 2 to about 20, and wherein said application of heat obtains from the mixture polyimide prepolymers having an average molecular weight in the range of about 2000 to about 10,000; and (2) heating the prepolymers to a temperature of at least about 690° F. to obtain polyimide resins having an average molecular weight in excess of 10,000.

14. A process for preparing polyimide resins comprising the steps of:

(1) heating a solution of solvent and from about 30 percent to about 90 percent by weight of a mixture of compounds of the following formulas:

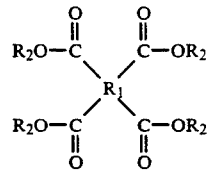
(a)

wherein $R_1$ is a tetravalent aryl radical substituted with a halogen selected from the group consisting of chlorine and fluorine, and $R_2$ is alkyl or hydrogen; and at least two $R_2$ are alkyl;

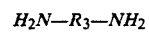
(b)

wherein $R_3$ is a divalent aryl radical; and

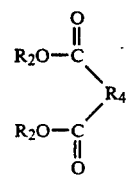
(c)

wherein $R_2$ is as defined in (a) and at least one $R_2$ is alkyl, and $R_4$ is a divalent radical of the formula:

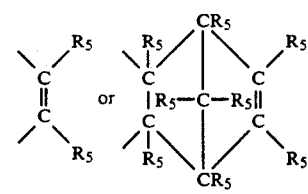

wherein $R_5$ is hydrogen or lower alkyl, and wherein the molar ratio of a:b:c: is n:n:1, wherein n is from 2 to about 20, wherein the solution is heated to a temperature sufficiently high to remove the solvent, the solvent being inert to the mixture, (2) thereafter heating the mixture to at least about 375° F. to obtain polyimide prepolymers having an average molecular weight in the range of about 2000 to about 10,000;

(3) heating the prepolymers to a temperature of from about 690° to about 750° F. for a sufficiently long time to obtain crosslinked thermally stable polyimide resin having an average molecular weight in excess of 10,000; and (4) curing the polyimide resin at a temperature of at least about 700° F. for at least 12 hours to improve the thermal stability and physical properties of the polyimide resin.

15. Thermally stable polyimide resin having an average molecular weight in excess of 10,000 prepared by the process of claim 12, 13, or 14.

16. An article of manufacture comprising fibers impregnating the polyimide resin of claim 15.

17. The polyimide resin of claim 15 having a $T_g$ greater than 600° F.

18. The polyimide resin of claim 17 having a weight loss of less than 10% when heated in air at 700° F. for 100 hours.

19. A process for preparing polyimide resins comprising the steps of:

(1) heating a solution of solvent and from about 30 percent to about 90 percent by weight of a mixture of compounds of the following formulas:

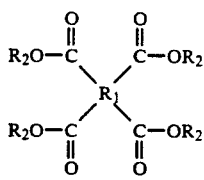  (a)

wherein $R_1$ is a tetravalent aryl radical substituted with a halogen selected from the group consisting of chlorine and fluorine, and $R_2$ is alkyl or hydrogen; and at least two $R_2$ are alkyl;

$NH_2-R_3-NH_2$  (b)

wherein $R_3$ is a divalent aryl radical; and (c) a divalent end cap compound characterized by (i) having at least one unsaturated moiety, (ii) being capable of reacting with the ester to form an end cap radical that precludes further reaction of the aromatic diamine with the ester, and (iii) being incapable of undergoing addition polymerization, and wherein the molar ratio of a:b:c: is (n+1):n:1, wherein n is from 2 to about 20, wherein the solution is heated to a temperature sufficiently high to remove the solvent, the solvent being inert to the mixture, (2) thereafter heating the mixture to at least about 375° F. to obtain polyimide prepolymers having an average molecular weight in the range of about 2000 to about 10,000;

(3) heating the prepolymers to a temperature of from about 690° to about 750° F. for a sufficiently long time to obtain crosslinked thermally stable polyimide resin having an average molecular weight in excess of 10,000; and (4) curing the polyimide resin at a temperature of at least about 700° F. for at least 12 hours to improve the thermal stability and physical properties of the polyimide resin.

20. The process of claim 12 or 13 comprising the additional step of curing the polyimide resins at a temperature of at least about 700° F. for at least 12 hours to improve the thermal stability and physical properties of the polyimide resins.

21. A polyimide resin having a molecular weight greater than 10,000 prepared by the steps of heating the composition of matter of claim 3 to form prepolymers having the formula of either (d) or (e), and cross-linking the formed prepolymers.

22. A polyimide resin having a molecular weight greater than 10,000 prepared by the steps of heating the composition of matter of claim 4 to form a prepolymer, and cross-linking the formed prepolymers.

23. An article of manufacture comprising fibers impregnating a polyimide resin matrix having a molecular weight greater than 10,000 and prepared by the steps of heating the composition of matter of claim 3 to form prepolymers having the formula of either (d) or (e), and cross-linking the formed prepolymers.

24. An article of manufacture comprising fibers impregnating a polyimide resin matrix having a molecular weight greater than 10,000 and prepared by the steps of heating the composition of matter of claim 4 to form a prepolymer, and cross-linking the formed prepolymer.

25. The polyimide resin of claim 21 or 22 having a $T_g$ greater than 600° F.

26. The polyimide resin of claim 25 having a weight loss of less than 10 percent when heated in air at 700° F. for 100 hours.

27. The composition of matter of claim 3 wherein monomer (a) is an ester of 4,4'-(hexafluoroisopropylidene)-bis(phthalic anhydride).

28. The composition of matter of claim 4 wherein compound (a) is an ester of 4,4'-(hexafluoroisopropylidene)-bis(phthalic anhydride).

* * * * *

UNITED STATES PATENT AND TRADEMARK OFFICE
CERTIFICATE OF CORRECTION

PATENT NO.   : 5,149,772
DATED        : September 22, 1992
INVENTOR(S)  : Serafini, et al.

It is certified that error appears in the above-indentified patent and that said Letters Patent is hereby corrected as shown below:

Column 13, lines 33 to 55, the formulas (d) and (e) should be aligned under column 14.

Column 15, line 56, for "n:n,1" read -- n:n:1 --;

Column 16, lines 55 and 56, strike out [$_2$N—R$_3$—NH$_2$].

Signed and Sealed this

Twelfth Day of April, 1994

BRUCE LEHMAN

Commissioner of Patents and Trademarks

Attest:

Attesting Officer